Figure 1:
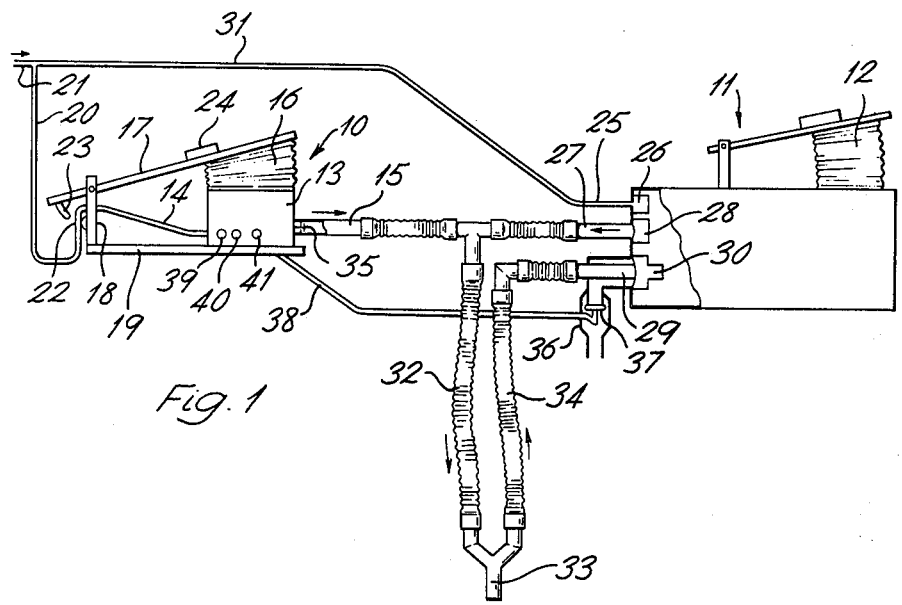

United States Patent [19]

Hewlett

[11] 4,176,663
[45] Dec. 4, 1979

[54] MEDICAL VENTILATION APPARATUS

[75] Inventor: Anthony M. Hewlett, Harrow, England

[73] Assignee: National Research Development Corporation, London, England

[21] Appl. No.: 839,381

[22] Filed: Oct. 4, 1977

[30] Foreign Application Priority Data

Oct. 5, 1976 [GB] United Kingdom .............. 41302/76

[51] Int. Cl.² ............................................ A61M 16/00
[52] U.S. Cl. ......................... 128/204.26; 128/205.16; 128/205.24
[58] Field of Search ............... 128/145.5, 145.6, 145.8, 128/188

[56] References Cited

U.S. PATENT DOCUMENTS

| | | | |
|---|---|---|---|
| 2,924,215 | 2/1960 | Goodner | 128/145.6 |
| 3,333,603 | 8/1967 | Manley | 128/145.6 X |
| 3,916,888 | 11/1975 | Buck et al. | 128/145.6 |
| 4,036,221 | 7/1977 | Hillsman et al. | 128/145.6 |

Primary Examiner—Henry J. Recla
Attorney, Agent, or Firm—Cushman, Darby & Cushman

[57] ABSTRACT

Medical ventilating apparatus is provided whereby gas is supplied to a patient at a preset volume flow rate, with the patient breathing spontaneously what he can from this flow, while the remaining gas is accumulated and forcibly delivered intermittently at preset volumes. The apparatus comprises a primary reservoir to hold gas at a constant pressure for spontaneous breathing, and a secondary reservoir in which accumulated gas is held for forced ventilation. Two basic forms of apparatus are possible in each of which one reservoir is filled up to a preset volume and forced ventilation is triggered when the other reservoir has also filled to a preset volume. In one form the reservoirs are connected in parallel and triggering is effected by the secondary reservoir, and in the other form the reservoirs are connected serially and triggering is effected by the primary reservoir.

11 Claims, 3 Drawing Figures

MEDICAL VENTILATION APPARATUS

Patients who have been artificially ventilated from a positive pressure ventilator often experience difficulty in re-establishing spontaneous breathing. In managing this problem in the past, use has been made of a so-called triggered ventilator, which is one arranged to deliver forcibly a preselected volume of gas when the patient attempts to inhale. However this procedure is not entirely satisfactory for several reasons. Recently a new procedure has been used, namely that of so-called intermittent mandatory ventilation, in which the patient is allowed to breathe spontaneously from a non-return gas supply while being, in addition, artificially ventilated by a positive pressure ventilator at preselected time intervals. This procedure neither takes into account the prevailing ability of the patient to breathe spontaneously, nor the timing of such breathing, so that he may often be artificially ventilated just when he is exhaling after a spontaneous breath.

An object of the present invention is to improve this situation, but before describing the invention it is useful to explain some of the terminology used hereinafter.

"Minute volume" is the mean flow of gas to the patients lungs.

"Tidal volume" is the volume of gas inhaled during one breath and may relate to the patient or a ventilator respectively to indicate the volume of a spontaneous or artificial breath.

A "minute volume dividing ventilator" is one which divides an incoming gas flow into discrete tidal volumes for intermittent delivery to the patient.

"Positive end expiratory pressure" is the lowest pressure at which exhalation can occur during artificial ventilation.

"Continuous positive airway pressure" is the corresponding pressure during spontaneous breathing.

Also it is appropriate to note that the term "gas" is used in the present context in its usual more general sense to embrace a mixture of gases.

Turning now to the invention, this involves a new procedure whereby gas is supplied at a preset volume flow rate to the patient, who spontaneously breathes from it what he can, and the remainder is accumulated, and delivered to the patient intermittently by use of a minute volume dividing ventilator.

Under this procedure the frequency of artificial ventilation is not preselected but is variable and determined by the patient's ability to breathe spontaneously. The frequency in question is additionally subject to the volume flow rate of the supply and the tidal volume of the ventilator, but these are preset and are therefore constant factors.

Moreover, since all of the gas breathed by the patient is derived from the same supply, whether breathing is spontaneous or artificial, the minute volume is constant and determined by the preset volume flow rate of the supply.

In order to enable this procedure to be carried out, the invention provides medical ventilation apparatus for connection with a supply of gas at a preset volume flow rate, said apparatus comprising: a constant pressure primary reservoir operable to receive gas from said supply and to deliver the same to a patient for spontaneous respiration; a secondary reservoir connected with said primary reservoir to receive excess of gas from said supply relative to that spontaneously inspired by said patient; and control means operable in response to accumulation of a preset volume of said excess to forcibly deliver gas to said patient from said second reservoir for artificial respiration.

Two basic forms of this apparatus have been developed so far. In a first form the secondary reservoir is connected in parallel with the primary reservoir, and the control means functions firstly to cause preferential filling of the primary reservoir with excess gas up to a preset volume, and secondly to cause forcible delivery of gas from the secondary reservoir when this has also filled to a preset volume. In the second form of the invention the secondary reservoir is connected serially with the primary reservoir and the control means functions firstly to cause preferential filling of the secondary reservoir with excess gas up to a preset volume, and secondly to cause forcible delivery of this volume when the primary reservoir has also been filled to a preset volume.

It will be appreciated that the secondary reservoir and the control means operate together under the second function of the latter as a minute volume dividing ventilator, but with the frequency of operation determined by the patients ability to breathe spontaneously as noted above. In fact existing minute volume dividing ventilators will usually incorporate reservoirs which can be used for the purposes of the invention to serve the role of the secondary reservoir and/or components which can serve part of the role of the control means required by the invention.

Also, since there are two reservoirs for delivery of gas to the patient which are respectively associated with different modes of breathing, it is appropriate that there should be no undesirable interaction therebetween. For example, it should not be possible for the primary reservoir to be charged with gas from the secondary reservoir when gas is forcibly delivered from the latter, and this requirement can be met by the provision of suitably located unidirectional valves. Similarly, it should not be possible for gas from either reservoir to by-pass the patient to atmosphere, and further valves can meet this requirement. However, these last valves must be compatible with the requirements for expiration during spontaneous and artificial breathing.

In this last connection a special valve has been developed for use with the invention, this valve serving to provide a by-pass inhibiting function while controlling the positive end expiratory pressure and corresponding continuous positive airway pressure. The valve in question comprises a valve member in the form of a resilient hollow capsule shaped to engage the valve seat so that the valve is normally closed. In use the capsule is connected to the primary reservoir and requires an opening pressure slightly higher than that of such reservoir due to the resilience of the capsule.

Since the invention has been developed so far with the use of commercially-available ventilators, and this serves to illustrate both the versatility of the invention and the requirements relevant to any further development of a special-purpose apparatus, it is appropriate to clarify the invention further with reference to this initial development.

Figure 2:
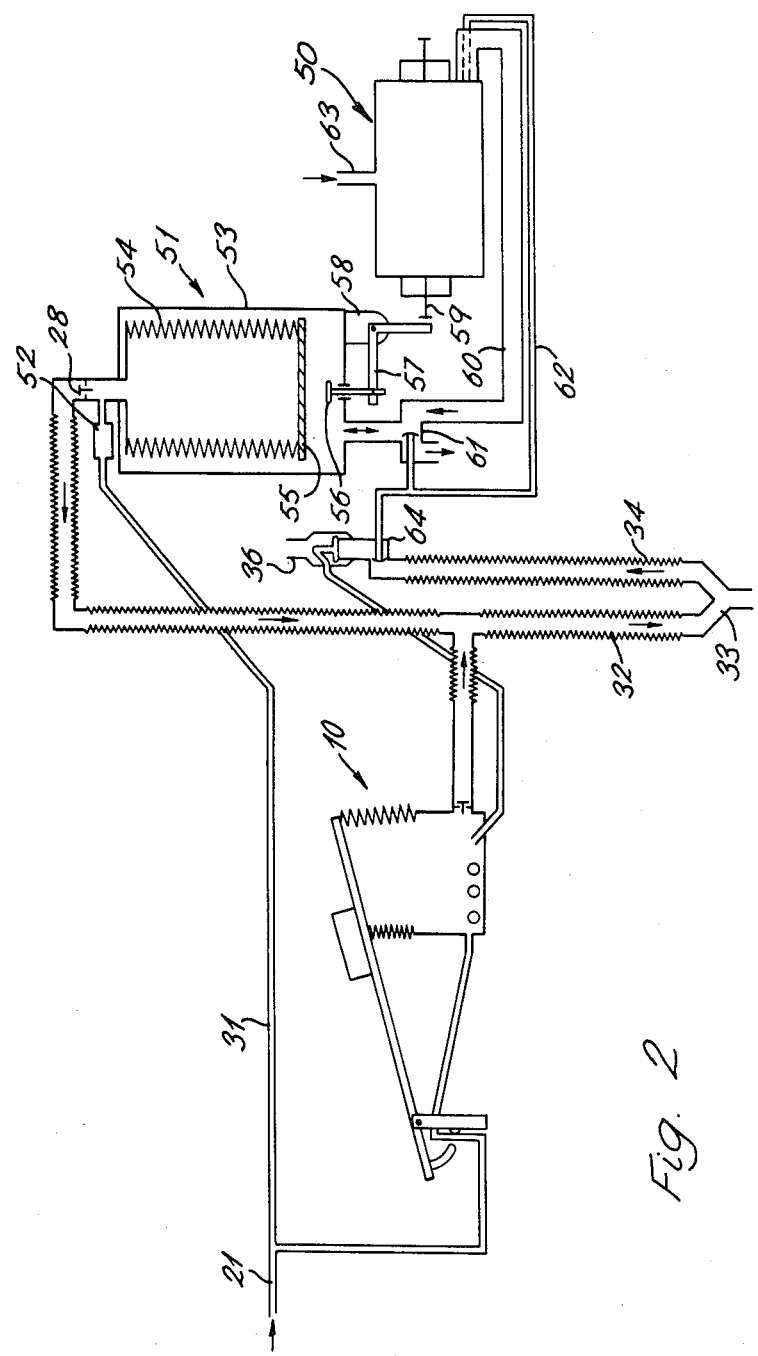

In this connection reference is made to the accompanying drawings, in which:

FIG. 1 schematically illustrates one embodiment of the first form of the invention;

FIG. 2 similarly illustrates another such embodiment; and

Figure 3:
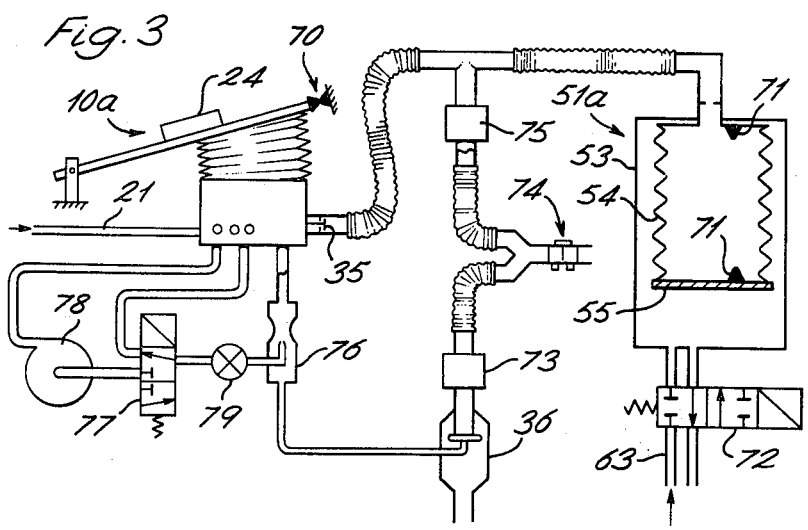

FIG. 3 schematically illustrates an embodiment of the second form of the invention.

In the embodiment of FIG. 1 the primary reservoir is denoted generally at 10 and a minute volume dividing ventilator at 11, the ventilator being of 'Brompton Manley' type and including a bellows 12 which serves as the secondary reservoir.

The primary reservoir comprises a base chamber 13 having an inlet 14 and an outlet 15, and to which a bellows 16 is fitted. The bellows 16 has its lower end open to the base chamber and its upper end connected to an arm 17 which is pivotally connected to a post 18 upstanding from a base plate 19 to which the base chamber is connected. The inlet 14 is connected by a pipe 20 to a flow-controllable gas source 21. A portion 22 of the pipe 20 is carried along the post 18 to face the free end of a finger 23 projecting from the end part of the arm 17 remote from the bellows 16.

At least the portion 22 of pipe 20 is resilient and the arrangement is such that the top of the bellows 16 describes a vertical arc upon being filled with gas, and pivots the arm 17 until the finger 23 engages and closes the pipe portion 22. This terminates filling of the bellows 16 to determine the maximum volume thereof, and this volume can be made variable by the provision of a suitably adjustable finger 23 if desired.

The pressure within the bellows 16 can be varied by the provision of a weight 24 on the arm 17, which weight is mounted for adjustment in location along the arm. The bellows can be such as to provide a substantially constant pressure in the primary reservoir as the bellows expand and contract, and the mechanical advantage of the lever action of the arm and finger, and the resilience of the pipe portion can be chosen so that only a relatively small increase in pressure occurs in the reservoir when its gas supply is cut off.

The Manley ventilator 11 conventionally operates automatically to deliver a preset tidal volume of gas when filled to the relevant volume, with both the volume and pressure being adjustable. The ventilator has a gas inlet 25 incorporating a normally-closed unidirectional valve 26, which opens in response to a pressurised gas supply, an outlet 27 incorporating a valve 28 which opens to allow ventilation, and houses an expiratory conduit 29 incorporating a valve 30 which is closed during artificial ventilation.

The gas source 21 is connected to the ventilator inlet by way of a pipe 31 and the inlet valve 26 is operable to open only in response to a pressure greater than the maximum for the primary reservoir content. Thus, the ventilator is charged only at times when the reservoir is full.

The outlets 15 and 27 from the primary reservoir and ventilator are connected to the patients airway through a common inspiratory tube 32, via a junction member 33 from which a common expiratory tube 34 leads to the ventilator conduit 29.

A unidirectional valve 35 is incorporated in the primary reservoir outlet to prevent charging of the reservoir by the ventilator, the reverse charging possibility being inhibited by the existing ventilator output valve 28.

It is also appropriate to prevent loss of gas from the reservoir by way of the inspiratory tube and expiratory tube when the valve 30 in the latter is open. A special valve 36 has been developed for this purpose and is connected to the expiratory tube at the outlet of the conduit 29. The valve 36 has a valve member in the form of a resilient hollow capsule 37 shaped to engage the valve seat, the capsule being connected to the primary reservoir by a pipe 38. The elasticity of the capsule is such as to maintain engagement with the seat, and so close the valve, when the pressure on the patients side of the valve is substantially the same as that within the capsule—this is the case in the absence of breathing. When the patient inhales the pressure in the expiratory tube is reduced and so the valve remains closed. In order for the patient to exhale, he must increase the pressure in the expiratory tube relative to that of the primary reservoir so that the valve opens, and expiration following operation of the ventilator must open the valve similarly. Thus the valve determines both the positive end expiratory and continuous positive airway pressures. The valve is isolated, by closure of the ventilator expiratory valve, from the high pressure developed during operation of the ventilator.

The remaining features of the embodiment of FIG. 1 concern matters of safety. A unidirectional valve 39 is provided in the reservoir base chamber to allow an air inflow from atmosphere if the pressure in the chamber falls below atmospheric pressure. This allows for the possibility that the patient's minute volume may temporarily exceed the volume flow rate of the gas supply and exhaust the reservoir.

Also, the reservoir base chamber is provided with a bleed passage 40 to atmosphere. This takes account of the fact that, if, for any reason, the reservoir outlet valve 35 becomes incompetent, the primary reservoir could become charged to an excess pressure by the ventilator with consequent hindrance to adequate exhalation by transmission of this pressure to the capsule of the special valve 36. This situation in fact will only occur when there is little or no spontaneous breathing.

As a further safeguard against excess pressure in the primary reservoir, a further relief valve 41 is provided in the base chamber to release large quantities of gas if the pressure increases significantly above the maximum settable pressure for the primary reservoir. As an indication of the relevant level of significance, an excess of about 1 cm water pressure is thought appropriate to a maximum of 15 cms water pressure.

The overall operation of the embodiment of FIG. 1 will be apparent from the foregoing description thereof and the preceding discussion of the invention.

However it is appropriate to note that artificial ventilation is unlikely to occur at the same time as exhalation during spontaneous breathing, since the latter breathing necessarily involves depletion of the primary reservoir and this reservoir must be refilled before the ventilator can operate.

Turning to the embodiment of FIG. 2: this differs from that of FIG. 1 by the separate provision of a secondary reservoir for operation by a minute volume dividing ventilator which does not normally include a reservoir but instead directly controls a high pressure gas supply to provide discrete tidal volumes therefrom. In the present case the ventilator in question is a Bird Mark 7 or 8 denoted at 50, the secondary reservoir is denoted generally at 51, and the primary reservoir is the same as in FIG. 1. Also it is necessary to provide a pressure-responsive check valve 52 as a control means to divert gas to the secondary reservoir.

The secondary reservoir 51 comprises a rigid chamber 53 inside which a bellows 54 is suspended. The bellows 54 carries a weight 55 at its base and is connected at its upper end to the gas supply 21 by way of the check valve 52. A plunger 56 is slidably mounted in the base of the chamber 53 in sealed manner, and a bellcrank lever 57 is pivoted on a flange 58 projecting from the chamber base. One arm of the lever 57 is adjustably coupled to the plunger 56 so that the effective height of the latter can be varied, and the other lever arm is disposed adjacent to the manual cycle control button 59 of the ventilator. The chamber 53 is connected to the ventilator outlet by way of a pipe 60 incorporating a standard Bird expiratory valve 61, such a valve being normally open to atmosphere, but being closed during ventilator operation by a pilot gas supply from the ventilator through a pipe 62.

Operation of this arrangement is such that, as before, when the primary reservoir 10 is full, excess gas from the supply 21 is diverted by the valve 52 to the secondary reservoir bellows 54. The weight 55 maintains a negative pressure in the bellows 54 relative to the interior of the chamber 53, which is opened to atmosphere by the valve 61, to retain valve 28 closed except during artificial ventilation. The bellows expands downwardly to fill and, when full, depresses the plunger 56 to rotate the lever 57, push the button 59, and initiate an operating cycle on the ventilator to discharge gas at high pressure, from its inlet 63, by way of pipes 60 and 62. The pilot supply in pipe 62 closes the valve 61 to atmosphere and conditions this valve to connect the pipe 60 wholly with the chamber 53, whereat the bellows 54 is deflated to artificially ventilate the patient by way of valve 28 and the common respiratory tube 32.

As in FIG. 1, a common expiratory tube 34 incorporating a special valve 36 is employed, and the function of valve 36 is effected by a further Bird valve 64.

Turning now to FIG. 3: it is convenient to describe this in two stages, with one stage concerning the differences which arise by virtue of the relevant embodiment being of the second form of the invention, and the other stage concerning additional features involving control of the positive end expiratory pressure.

The embodiment of FIG. 3 comprises various components corresponding to those of the previous two embodiments and the same reference numerals are employed where appropriate. Also, the primary and secondary reservoirs are respectively similar to the reservoir 10 and the reservoir of the ventilator 51 above, and so the former are generally denoted as 10a and 51a to facilitate comparison. A principal difference in FIG. 3, however, is that the two reservoirs are connected serially to the supply 21, with the reservoir 51a downstream from 10a, and so the primary reservoir has no means for diverting the supply to the secondary reservoir. Other differences occur in the control means which, in this instance, comprise switches 70 and 71 or similar electrical signal trigger devices respectively connected with the primary and secondary reservoirs and operated by the same to control a solenoid valve 72 which controls, in turn, the delivery from the secondary ventilator. It will be seen that switch 70 operates when the primary reservoir is filled to predetermined volume, switch 71 operates when the secondary reservoir is emptied and the valve 72 has a normal and operated state in which the chamber 53 of reservoir 51a is respectively open to atmosphere and subject to the pressurised gas supply from the pipe 63. Switch 70 operates to change the valve 72 from its normal state, and switch 71 operates to change the valve 72 back to its normal state.

Operation of this embodiment will usually commence from a condition in which the primary reservoir is empty and the secondary reservoir is full of air or gas from the supply 21. The secondary reservoir is full at this time by virtue of the chamber 53 being open to atmosphere and the bellows 54 being subjected to a negative pressure by the weight 55, and this reservoir can be filled with gas by initially purging air from the apparatus. During operation the gas supply will charge the primary reservoir 10a and the patient draws gas from this reservoir for spontaneous respiration by virtue of its positive pressure due to the weight 24. Any excess of the gas supplied relative to that breathed spontaneously accumulates in the primary reservoir until the switch 70 is operated, whereupon the valve 72 is changed over and the patient is artifically ventilated from the secondary reservoir until the latter is emptied and switch 71 opeates to change valve 72 back to its normal state. It will be noted that the valve 35 prevents the secondary reservoir charging the primary reservoir during artificial ventilation, but the primary reservoir continues to receive gas from the supply 21. After artificial ventilation the secondary reservoir is filled from the primary reservoir and the supply, although this does not inhibit supply to the patient for spontaneous breathing.

Expiration is effected through a positive end expiratory pressure valve 36 of the kind described above, and this valve is protected against the inspiratory gas flow during artificial ventilation by a servo valve 73 which is closed by switch 70 and opened by switch 71.

The further differences in FIG. 3 centre on the use of a sensor 74 located in the junction member 33, which sensor operates to generate electrical signals distinguishing between periods of inspiration and expiration. This sensor can be of any appropriate form, but uitably comprises a flap within the member which flap is biassed to a datum position extending transversely therethrough, but is moved from this position in respectively opposite senses in response to gas flow during inspiration and expiration. The signal outputs can be produced by locating photocells adjacent opposite sides of the flap so that flap movement masks one or other photocell relative to an opposed light source. This sensor serves to open and close a further servo valve 75 during inspiration and expiration, respectively, valve 75 being located in the common tube 32 from the reservoirs to the member 33. In addition, the sensor serves to control the operational pressure of the capsule in valve 36. For this last purpose the capsule is supplied with gas as before from the primary reservoir but by way of a pressure regulator 76. This regulator comprises a venturi tube through which gas from the primary reservoir passes to the capsule of valve 36, and also a nozzle projecting into the venturi restriction against the gas flow. This nozzle is itself connected to the primary reservoir, by way of a solenoid valve 77, either directly or in series with a pump 78. The valve 77 normally connects the nozzle in the former manner during inspiration and the nozzle is subject to gas flows of like pressures in opposite directions and therefore does not modify the capsule pressure significantly. However, the valve is operated to its other state by the sensor 74 during expiration so that the nozzle receives a pressurised gas supply from the pump 78 and accordingly reduces the pressure applied to the capsule. The gas supply to the regulator nozzle from the valve 77 is preferably passed through a regulator valve 79 to allow adjustment of the positive end expiratory pressure.

While the invention has been more particularly described with reference to the illustrated embodiments it is not intended to be limited by these. Indeed, it is clear from the differences between these embodiments that variation is possible in practical application of the invention, and further variations are possible. For example, use of a sensor to regulate the positive end expiratory pressure by control from a respiration sensor is possible with embodiments other than that of FIG. 3. Also, the embodiments illustrate the versatility of the invention in its ability to employ the same by augmenting existing equipment, and also clearly indicate that additional, conventional modes of ventilation can be effected with sub-combinations of components of the overall apparatus. Thus the primary ventilator can be used with its directly associated components to provide assisted ventilation at a preset constant pressure. Similarly, the ventilator can be used to provide artificial ventilation which can be of minute volume dividing or other form and be subject to controlled positive and expiratory pressure determined by the primary reservoir.

We claim:

1. Medical ventilation apparatus comprising: a pre-set volume flow rate supply of gas, a constant pressure primary reservoir having a first preselected volume connected to said supply, gas delivery means connected to said primary reservoir to convey gas therefrom to a patient on demand for spontaneous respiration, a secondary reservoir having a second preselected volume, means for passing any excess of gas from said supply to said primary reservoir over said first preselected volume to said secondary reservoir, said secondary reservoir being connected to said delivery means, control means operable in response to accumulation of said first preselected volume of gas in said primary reservoir and said second preselected volume of gas in said secondary reservoir to forceably deliver gas to the patient from said secondary reservoir for artificial respiration.

2. Apparatus according to claim 1 wherein said primary reservoir comprises an inlet valve operable to open to atmosphere in response to sub-atmospheric pressure within such reservoir.

3. Apparatus according to claim 2 wherein said primary reservoir comprises a bleed outlet open to atmosphere.

4. Apparatus according to claim 2 wherein said primary reservoir comprises a relief valve operable to open to atmosphere in response to a predetermined pressure therein greater than said constant pressure.

5. Apparatus according to claim 1 wherein an expiratory path is provided from said patient which comprises a valve including a resilient hollow capsule normally engaged with the valve seat, said capsule being connected to said primary reservoir for receipt of gas.

6. Apparatus according to claim 5 wherein said gas supply connection to said capsule comprises a pressure regulator operable to change the pressure of such supply between a higher value and a lower value in response to inspiration and expiration by said patient respectively.

7. Apparatus according to claim 5 wherein said expiratory path comprises a normally-open valve operable to close in response to delivery of gas from said secondary reservoir.

8. Apparatus according to claim 1 wherein said primary and secondary reservoirs are connected serially with said supply, and said control means functions firstly to cause preferential filling of said secondary reservoir with said excess gas up to a preset volume, and secondly to cause forcible delivery of this volume when the primary reservoir has also been filled to a preset volume.

9. Medical ventilation apparatus comprising: a pre-set volume flow rate supply of gas, a constant pressure primary reservoir having a first preselected volume connected to said supply, gas delivery means connected to said primary reservoir to convey gas therefrom to a patient on demand for spontaneous respiration, a secondary reservoir having a second preselected volume, means for passing any excess of gas from said supply to said primary reservoir over said first preselected volume to said secondary reservoir, said secondary reservoir being connected to said delivery means, control means operable in response to accumulation of said first preselected volume of gas in said primary reservoir and said second preselected volume of gas in said secondary reservoir to forceably deliver gas to the patient from said secondary reservoir for artificial respiration, and a patient supply outlet from each of said reservoirs each having a respective non-return valve.

10. Medical ventilation apparatus comprising: a pre-set volume flow rate supply of gas, a constant pressure primary reservoir connected to said supply, gas delivery means connected to said primary reservoir to convey gas therefrom to a patient on demand for spontaneous respiration, a secondary reservoir having a second preselected volume, means for passing any excessive gas from said supply to said primary reservoir over said first preselected volume to said secondary reservoir, said secondary reservoir being connected to said delivery means, control means operable in response to accumulation of said first preselected volume of gas in said primary reservoir and said second preselected volume of gas in said secondary reservoir to forceably deliver gas to the patient from said secondary reservoir for artificial respiration, said control means including means firstly causing preferential filling of said primary reservoir with said gas up to said first preselected volume and secondly causing forceable delivery of gas from said secondary reservoir when said secondary reservoir has also filled to said second preselected volume.

11. A method of ventilating a patient which comprises supplying a gas at a pre-set volume flow rate into a primary reservoir having a first preselected volume, allowing said patient to breathe spontaneously what he can from such gas, accumulating the excess of said gas supplied to said primary reservoir over said first preselected volume and relative to that spontaneously inspired by said patient into a secondary reservoir having a second preselected volume, forceably ventilating said patient from said secondary reservoir when said excess gas therein accumulates to said second preselected volume.

* * * * *